United States Patent [19]
Gerhardt et al.

[11] Patent Number: 5,638,593
[45] Date of Patent: Jun. 17, 1997

[54] METHOD FOR MANUFACTURING A HEAT-SEALED NEO-NATAL MEDICAL MONITORING PROBE

[75] Inventors: Thomas J. Gerhardt, Littleton; Daniel Goldberger, Boulder; Dena M. Raley, Louisville; James H. Taylor, Boulder; Timothy A. Turley, Highlands Ranch; Kirk L. Weimer, Superior, all of Colo.

[73] Assignee: Ohmeda Inc., Liberty Corner, N.J.

[21] Appl. No.: 506,755

[22] Filed: Jul. 26, 1995

Related U.S. Application Data

[62] Division of Ser. No. 285,491, Aug. 3, 1994, abandoned, which is a continuation of Ser. No. 117,914, Sep. 7, 1993, abandoned.

[51] Int. Cl.$^6$ .............................. H05K 13/00; A61B 5/00
[52] U.S. Cl. ................... 29/592.1; 156/308.4; 156/313; 128/633; 356/41
[58] Field of Search .................... 29/592.1, 595, 29/609.1; 264/272.11, 272.14, 272.15, 272.16, 275; 156/308.4, 312, 313; 53/455, 467, 477; 128/633, 664, 665, 666; 356/41

[56] References Cited

U.S. PATENT DOCUMENTS

| | | | |
|---|---|---|---|
| Re. 34,599 | 5/1994 | Suszynski et al. | 128/664 X |
| 3,625,414 | 12/1971 | Caiola | 156/308.4 X |
| 4,036,211 | 7/1977 | Veth et al. | 128/666 X |
| 4,512,830 | 4/1985 | Hulett et al. | 156/308.4 X |
| 4,825,872 | 5/1989 | Tan et al. | 128/633 |
| 4,830,014 | 5/1989 | Goodman et al. | 128/666 |
| 4,865,038 | 9/1989 | Rich et al. | 128/665 |
| 4,928,691 | 5/1990 | Nicolson et al. | 128/633 |
| 4,974,591 | 12/1990 | Awazu et al. | 128/633 |
| 5,090,410 | 2/1992 | Saper et al. | 128/633 |
| 5,094,240 | 3/1992 | Muz | 128/633 |
| 5,170,786 | 12/1992 | Thomas et al. | 128/633 |
| 5,217,013 | 6/1993 | Lewis et al. | 128/633 |
| 5,247,932 | 9/1993 | Chung et al. | 128/633 |

FOREIGN PATENT DOCUMENTS

| | | |
|---|---|---|
| 0127947 | 12/1984 | European Pat. Off. . |
| 3809084 | 9/1989 | Germany . |

*Primary Examiner*—S. Thomas Hughes
*Attorney, Agent, or Firm*—Roger M. Rathbun; Larry R. Cassett; James M. Graziano

[57] ABSTRACT

A method for manufacturing a heat-sealed neo-natal medical monitoring probe requires a pair of light sources and a light detector to be placed between two layers or conformable material used to implement the probe. The layers are designed to be self-aligning when placed in the assembly press for heat-sealing the perimeter of the probe. The heat-sealing process both protects the light sources and detector from fluids and also functions to precisely position and secure these devices.

19 Claims, 5 Drawing Sheets

METHOD FOR MANUFACTURING A HEAT-SEALED NEO-NATAL MEDICAL MONITORING PROBE

This is a division of application Ser. No. 08/285,491 filed Aug. 3, 1994, now abandoned which in turn is an FWC of application Ser. No. 08/117,914 filed Sep. 7, 1993, now abandoned.

FIELD OF THE INVENTION

This invention relates to medical monitoring devices and, in particular, to a neo-natal probe that is designed to be efficiently manufactured to create a probe that is simple to use, inexpensive, easily conformed to the patient's appendage and sealed to enable it to be cleaned for reuse.

Problem

It is a problem in the field of medical monitoring apparatus to manufacture a probe that satisfies a number of diverse and sometimes contradictory requirements. It is important that the probe be simple to use, in that it conforms to a variety of patients who differ in size and shape. The probe must be securely affixable to the patient, such as on a patient's appendage, without requiring complex structures or elements that can irritate the patient. In addition, the probe must be either inexpensive so that it can be disposable after one use or able to be cleaned so that it can be used for many patient applications. If the probe is reusable, then the active elements contained therein that perform the sensing and measuring functions must be protected from the ambient environment and, likewise, it is a requirement that the patient be shielded from any potentially dangerous electrical signals or heat produced by the probe. The probe must also reliably and accurately perform the required measurements. The method of manufacture must therefore be efficient to minimize the cost of the probe and yet simple to ensure that the probe is reliable in its operation.

The reliability of an object is a function of the number of components contained therein, their respective re liabilities, as well as the complexity of the structure that is produced. It is therefore beneficial to provide a probe that uses a minimum number of components as well as a minimum number of steps in its assembly process. The assembly process should also be designed to enable the probe to be accurately manufactured without requiring the use of complex manufacturing apparatus or processes.

In the field of medical monitoring apparatus, a difficult probe to produce is a neo natal probe that is used for pulse oximetry measurements. These probes are typically affixed to the baby's foot, wrapped around the instep, since this site is both highly vascularized and of a geometry that provides sufficient structure to enable the probe to be securely affixed to the infant. Many of the existing neo-natal pulse oximetry probes are not reusable and therefore result in a significant additional expense in the hospital environment for monitoring neo-natal patients. The reusable neo-natal probes tend to be bulky and are difficult to conform to the size and shape of the infant being monitored. In addition, these probes are affixed to the instep of the infant by means of an integral adhesive strip which results in the probe being disposed of if the adhesive loses its ability to securely affix the probe to the infant, even though the probe is still functioning, thereby causing unnecessary additional costs. Some probes can have the adhesive strip replaced, but this is a difficult process and potentially not cost effective. These problems are all well-known in the field of medical monitoring apparatus, and numerous neo-natal probe designs are presently available on the market, all of which are similar in design but none of which solve the above-noted problems.

Solution

The above-described problems are solved and a technical advance achieved in the field by the neo-natal probe of the present invention which is implemented using a minimum number of components in a sealed enclosure. The probe consists of a pair of light sources and a light detector which are placed between two of the plurality of layers of the conformable material used to implement the probe. The layers are designed to be self-aligning when placed in the assembly press for heat-sealing the perimeter of the probe. The heat-sealing process both protects the light sources and detector from fluids and also functions to precisely position and secure these devices.

This probe may be reusable, thereby amortizing its cost over many patient applications. Furthermore, the probe is a minimalistic design to reduce its mass, thereby making it more easily conformed to the patient's appendage which is the instep of a neo-natal infant. The probe incorporates a replaceable adhesive strip so that the probe can be resecured to a patient many times with the adhesive being replaced whenever the adhesiveness of this strip becomes inadequate to maintain the probe securely affixed to the patient. Thus, this probe architecture overcomes the problems inherent in existing probes and also is architected for ease of reliable and accurate manufacture. This probe architecture therefore represents a significant advance in the crowded technology of neo-natal probes.

DETAILED DESCRIPTION

Figure 1:
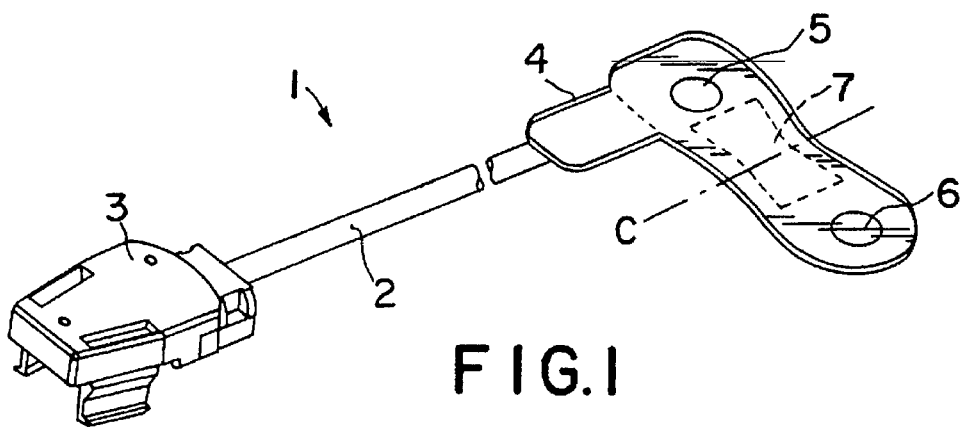
FIG. 1 illustrates a perspective view of the neo-natal probe of the present invention.

A pulse oximeter is frequently used to monitor the condition of a neo-natal patient. The pulse oximeter measures the oxygen saturation of the blood and produces a human readable display that indicates the patient's heart rate and saturation of the arterial blood. These readings are important to enable the medical staff to determine whether the patient's respiratory system is functioning properly, supplying sufficient oxygen to the blood. This is frequently a concern in neo-natal patients who often are given supplementary oxygen because they are unable to obtain sufficient oxygen intake through the lungs during normal respiration.

A pulse oximeter instrument operates by transilluminating a portion of the patient's anatomy that is rich in arterial blood and measuring the amount of light that is absorbed by the arterial blood to thereby determine oxygen saturation of the blood. The pulse oximeter makes use of a pair of light-emitting diodes, each of which transmits light at a predetermined wavelength, which wavelengths are selected to be highly absorbed by oxygenated hemoglobin in the arterial blood and reduced hemoglobin in the arterial blood, respectively. The amount of absorption of the light beams generated by these light emitting diodes is a measure of the concentration of the oxygenated and reduced hemoglobin in the arterial blood. On a neo-natal patient, the foot is an area that is highly vascularized and of a configuration that permits the connection of the light-emitting diodes to one side of the instep and a light detector to the other side of the instep to thereby transmit the two wavelengths of light through the arterial blood and measure the respective transmitted intensities thereof. The absorption of the light that is transmitted through the heel of the neo-natal patient includes a constant portion that is a result of skin, bone, steady-state blood flow and light loss to various other factors. The pulsatile component is a small fraction of the received signal and is used by the pulse oximeter system to perform its measurements. The measurements are computed by periodically sampling the output of the light detector to determine the incremental change in absorption of the two wavelengths of light transmitted through the instep of the neo-natal patient. These incremental changes in light absorption are then used to compute the oxygen saturation of the arterial blood as well as the infant's pulse rate. Since the received signals represent only a small fraction of the transmitted light, it is important that the incident light be of significant magnitude to result in signals that have sufficient amplitude to provide accurate readings. In addition, the light-emitting diodes and the light detector must be placed in intimate contact with the skin of the patient on opposite sides of the instep to obtain the most accurate readings. The probe design must therefore be such that it inherently accommodates variations in size and shape of the instep of the neonatal patient and also enables the medical staff to simply align the probe as well as properly align the probe to obtain the maximum readings. These stringent requirements are difficult for existing probes to comply with and increase the cost of the probes, which are disposable elements.

Probe Architecture

Any improvements in the design and manufacturability of the probe, however incremental, result in significant cost savings. The neo-natal probe 1 of the present invention is illustrated in perspective view in FIG. 1 and in perspective exploded view in FIG. 2. This neonatal probe 1 represents an architecture in which the configuration of elements are cooperatively operative to solve the problems of existing neo-natal probes and which render the probe reusable, thereby amortizing the cost of this probe over many patient applications. The neo-natal probe 1 includes a cable 2 that extends from a connector 3 to the sensor elements 17, 18 which are located in the sensor section 4. The cable 2 includes a plurality of electrical conductors, each of which is terminated on a corresponding conductive element contained within the connector 3. The connector 3 is designed to securely interconnect the cable conductors 2 with the medical monitoring instrument (not shown) to enable the medical monitoring instrument to transmit drive signals to the light-emitting diodes contained in the light source element 17 and to receive the signals that are output by the light detector 18. The sensor elements section 4 of the probe 1 is a unitary structure that consists of a plurality of layers of conformable material 11–16 that are used to enclose the light-emitting diodes 17 and light detector 18 and to perform various ancillary functions that are described herein below. The two light-emitting diodes in light source 17 and the light detector 18 are connected to corresponding conductors of the cable 2 and form the active elements used to perform the arterial blood monitoring function. The remaining elements illustrated in FIG. 1 and 2 represent the apparatus that is used to position, align, affix and isolate these active sensor elements 17, 18.

The assembled neo-natal probe 1 is illustrated in perspective view in FIG. 1 and consists of the assembled sensor section 4, the conductor cable 2 and the connector 3 that is affixed at the distal end thereof. The sensor section 4 consists of a sealed housing that provides a moisture barrier and an electrical barrier to prevent the exchange of contaminants or electrical signals between the sensor elements 17, 18 and the ambient environment that is extant around the probe. This seal extends to the cable 2 to completely seal the sensor section 4. The sealing process disclosed herein is a heat sealing process although other sealing processes, such as adhesive, ultrasonic bonding, etc. can be used dependent on the nature of the materials used to implement the layers of sensor section 4. The sealed sensor section 4 protects sensor elements 17, 18 from fluids, such as the cleaning and disinfectant fluids used on the probe prior to its reuse. The two circles 5, 6 illustrated on one side of the sensor section 4 represent the optical ports through which the light beams produced by the light-emitting diodes 17 are transmitted and the light received from the passage of these light beams through the patient's appendage is measured by the light detector 18, respectively. The area around the butterfly-shaped area 7 between these two light ports 5, 6 is an adhesive element that is used to adhesively affix the neo-natal probe 1 to the instep of the patient. In use, the ends of the neo-natal probe 1 are folded together to form a U-shaped structure, folded around the center line C illustrated in FIG. 1. This U-shaped configuration enables the neo-natal probe center section to conform to the shape of the instep of the patient and the integral adhesive secures the sensor section 4 to the instep of the neo-natal patient. This unitary structure is therefore simple in architecture, self-contained in that it may not require the use of adhesive strips that must be wrapped around the foot of the neo-natal patient, and not of a bulky construction that is difficult to apply and secure to the patient.

Multi-Layer Structure

Figure 2:
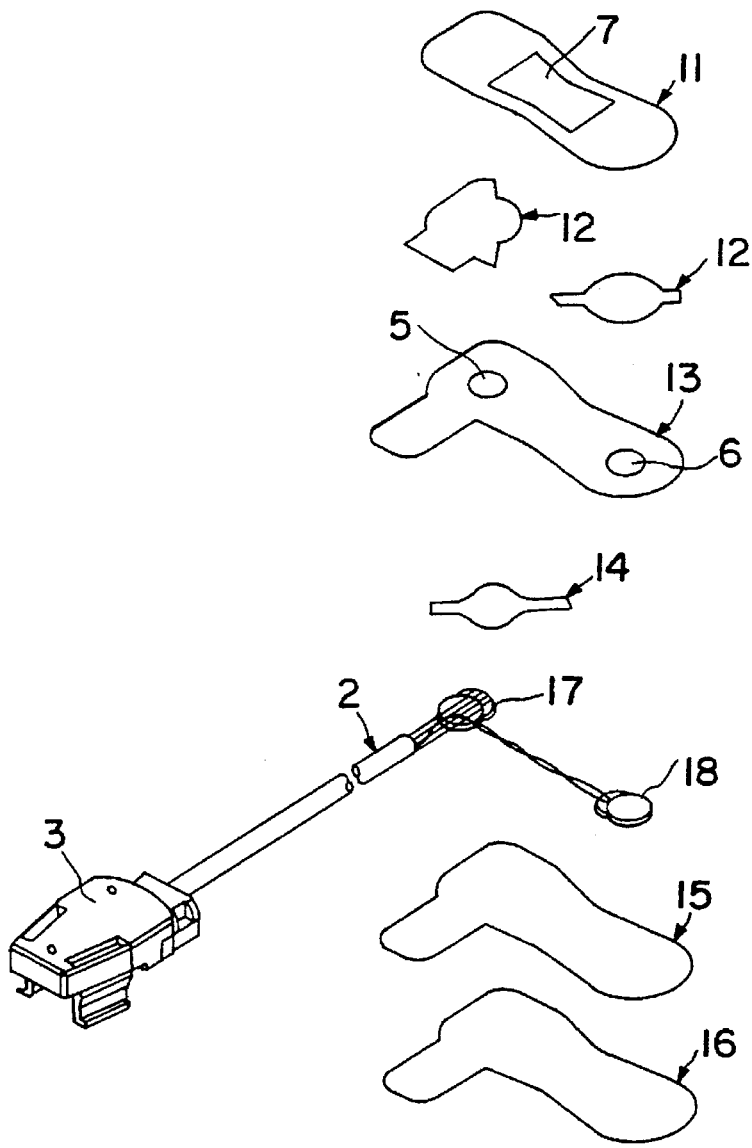
FIG. 2 illustrates a perspective view an exploded view of the neo-natal probe of the present invention.
Figure 4:
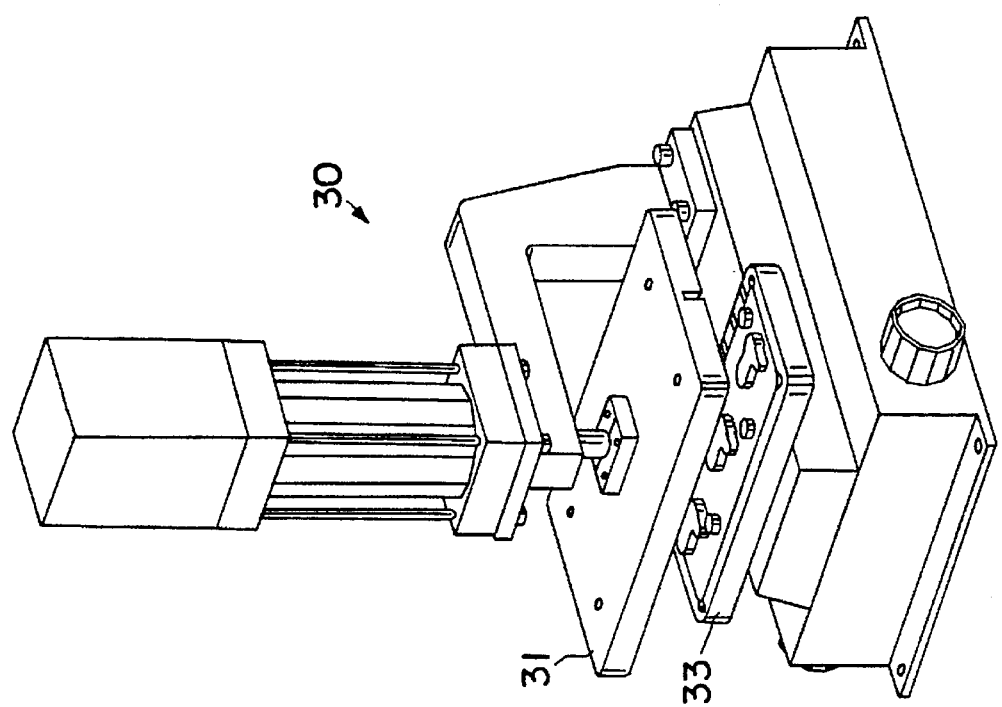
FIG. 4 illustrates a perspective top view of the apparatus used to manufacture the neo-natal prob of the present invention.
Figure 3:
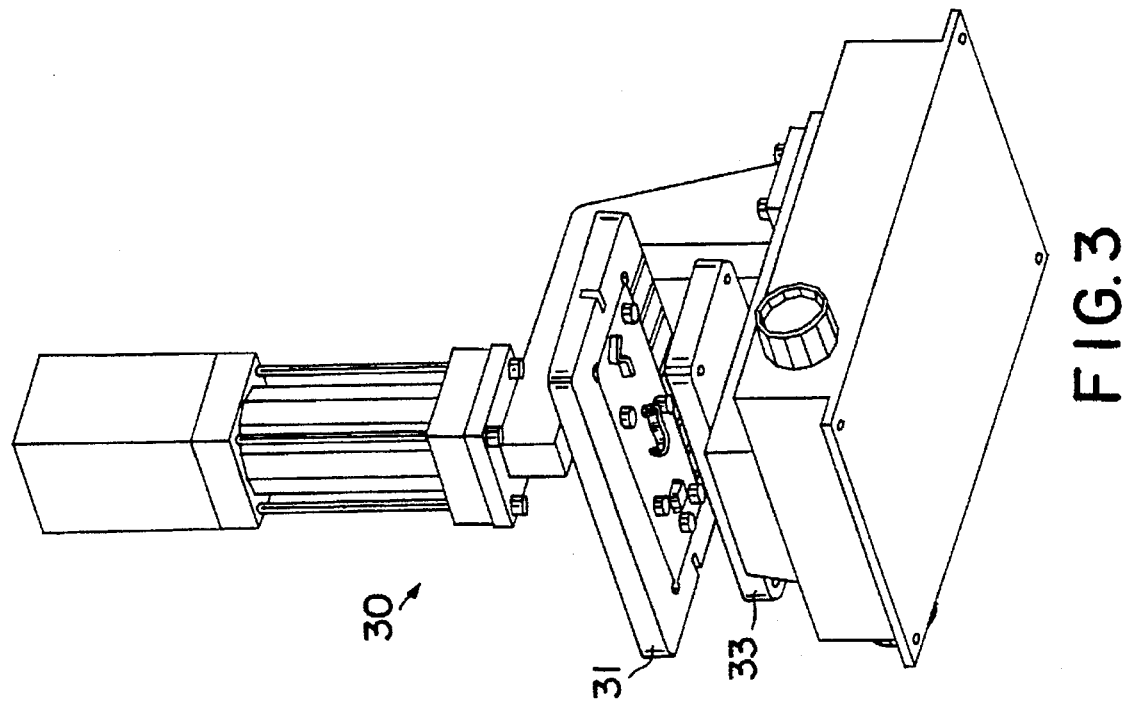
FIG. 3 illustrates a perspective bottom view of the apparatus used to manufacture the neo-natal probe of the present invention.
Figure 6:
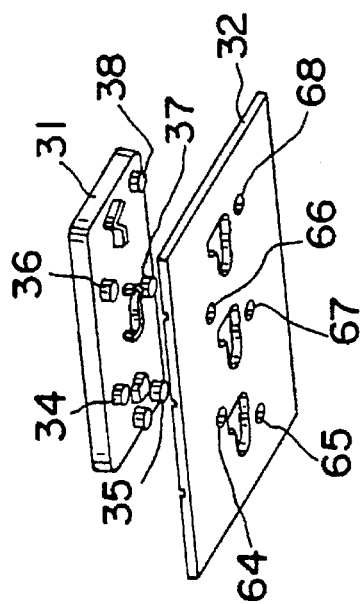
FIG. 6 illustrates a perspective view of the tooling plates used in the bottom segment of the press used to manufacture the probe of the present invention.
Figure 7:
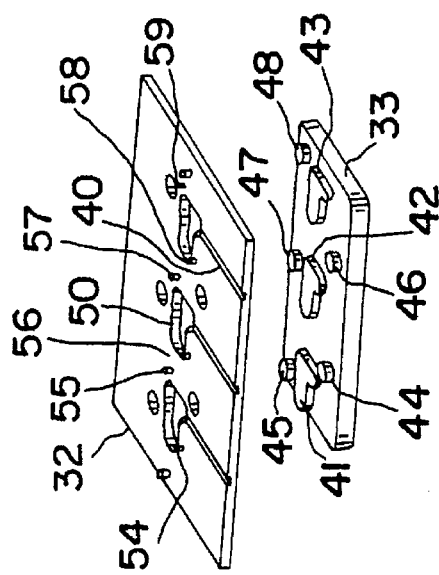
FIG. 7 illustrates a perspective view of the tooling plates used in the press used to manufacture the neo-natal probe of the present invention.
Figure 5:
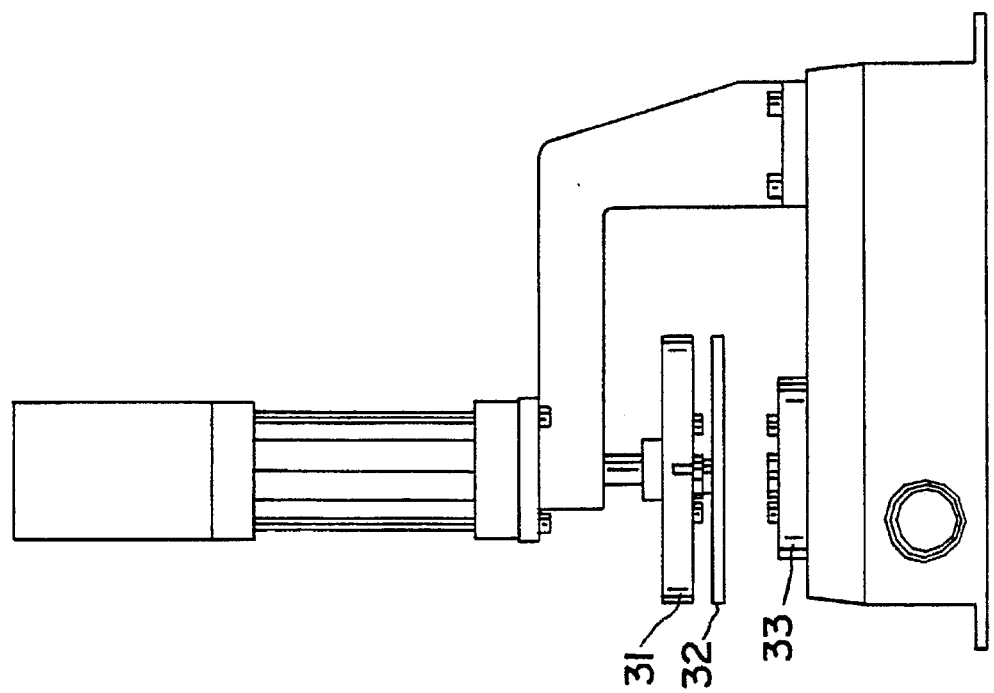
FIG. 5 illustrates a side view of the apparatus used to manufacture the neo-natal probe of the present invention.

The elements used to implement the sensor section 4 illustrated in FIG. 1 are shown in exploded view in FIG. 2. The light-emitting diodes 17 are selected to produce a high-intensity beam of light of predetermined wavelength to perform the required pulse oximetry measurements. In order to produce sufficient light output, the light-emitting diodes 17 must be fairly high-powered devices and generate a certain amount of thermal output in conjunction with their optical output. In order to prevent this thermal output from being a source of irritation to the patient, a thermal buffer 14 is placed over the light-emitting diodes 17 to thermally isolate the patient's appendage from the light-emitting diodes 17. This thermal buffer 14 must be optically transmissive and yet thermally insulative. In order to accomplish this, the thermal buffer 14 is manufactured from clear Kraton G film and is selected to be of extent to cover the light-emitting diodes 17 but yet limited in extent so as not to add significant mass to the sensor element section 4. It is important to prevent the light that is produced by the light-emitting diodes 17 from directly reaching the light detector 18, since this incident light is of sufficient magnitude to cause difficulty in detecting the desired pulsatile component of the light transmitted through the patient's appendage. Therefore, a layer of optically translucent material 13 is next applied over the light-emitting diodes 17 and light detector 18. The multiple layers, when sealed together in the manufacturing process, provide a light dam to block the sideways transmission of the light produced by the light-emitting diodes 17 and to focus the light output of the light-emitting diodes 17 in a direction to be incident on the skin of the patient. This optically translucent material is manufactured from a pink Kraton G film, and this element 13 is o size and dimension that matches the resultant size and dimension of the exterior package of the sensor element section 4. The next successive elements that are added to this structure are a pair of port covers 12 implemented from clear Kraton G film and used to insulate the light-emitting diodes 17 and light detector 18 from the ambient environment and yet provide optically transmissive paths from the light-emitting diodes 17 to the ambient environment. The final element 11 affixed to this succession of previously-listed elements is an adhesive face manufactured from clear single-sided adhesive polyethylene film which functions to provide the adhesive area required to affix the sensor 1 to the patient as well as to provide a layer used to sandwich the port covers 12 against the optical ports 5, 6 of the inner layer 13 previously described. On the bottom of the light-emitting diodes 17 and light detector 18 are placed two layers 15, 16, the first layer 15 being an optically opaque or translucent layer such as that manufactured from a pink Kraton G film used to prevent the intrusion of ambient light therein. The size and dimensions of this layer 15 are selected to match the size and dimensions of the exterior final dimensions of the sensor element section 4. Finally, a back face 16 manufactured from a polyethylene coextrusion overlies the optical buffer layer 15 to provide the outward facing cover which is subject to the greatest wear since it is the surface that is exposed to the ambient once the sensor 1 is affixed to the instep of the neo-natal patient. These various layers 11–16 are stacked together and heat-sealed around the perimeter of the optical ports 5, 6 to provide a light dam and heat sealed around the perimeter of sensor element section 4 using the apparatus described herein below. The resultant integrated structure is lightweight, simple in construction and yet provides a moisture- and light-resistant housing to enclose the light-emitting diodes 17 and the light detector 18. These various layers electrically isolate the light-emitting diodes 17 and light detector 18 from the patient's skin and yet provide an optically transmissive path to allow the generated light beams to be applied to the desired locus on the patient's instep and to receive the light that exits the patient's skin as a result of the transillumination of the arterial bed by the incident selected two wavelengths of light.

Probe Manufacturing Apparatus

FIGS. 3–7 illustrate various views of the apparatus that is used to manufacture the sensor 1illustrated in FIGS. 1 and 2. The manufacturing apparatus 30 makes use of three tooling plates 31–33 to position, sandwich and heat-seal the sensor element section 4 of the neo-natal probe 1 in a three-step process. As can be seen from these figures, the top plate 31 contains heat-sealing elements of three differing configurations. In operation, the top 31 and bottom 33 plates are affixed to the top and bottom sections of the apparatus 30 which forms a press that is operated by an appropriate activation means, such as compressed air, hydraulics, mechanical action, etc., to press the top 31 and bottom 33 plates together to thereby sandwich the various layers illustrated in FIG. 2 together and heat-seal a predetermined extent of the periphery of the sensor element section 4 illustrated in FIG. 1 and 2. The middle plate 32 of this apparatus is used to position the cable 2 and light-emitting diodes 17 and light detector 18 elements and to controllably enable the heat-sealing element to seal the housing layers thereto without damaging the conductors contained therein. The middle plate 32 also functions as a carrier to enable a worker to position the various elements that comprise probe 1 without having to come into contact with top 31 and bottom 33 plates with their heating elements. As can be seen from these figures, the top 31 and bottom 33 plates include height stops 34–38, 44–48 which are used to controllably position top 31 and bottom 33 plates with respect to each other when press 30 is closed. Middle plate 32 is equipped with alignment pins 54–59 which are used to position the various layers illustrated in FIG. 2 in precise alignment. The middle plate 32 contains a slot 40 used to accept the cable 2 and an oval-shaped opening 50 into which the light-emitting diodes 17 and light detector 18 are positioned as shown in FIG. 2.

In order to provide simplicity of alignment, the layers 11–16 illustrated in FIG. 2 are created using layers of greater extent (as shown in FIGS. 8–18) than shown in FIG. 2 and which include preformed apertures therein that correspond to and align with the alignment pins 54–59 shown on the middle plate 32 of the manufacturing apparatus. Thus, the layers 11–16 shown in FIG. 2 illustrate the heat-sealed and finally trimmed configuration of the various elements rather than the raw material that is used to manufacture the neo-natal probe 1. As each manufacturing step is completed, the subassembly is moved from left to right from land area to successive land area on bottom plate 33 until the final heat-sealing operation takes place on the third 43 or rightmost land area illustrated in FIGS. 3–7. It is obvious that this three-step process can be performed manually or is susceptible to automation with the various untrimmed layers 11–16 illustrated in FIGS. 8–18 being part of a continuous-feed roll material sequenced through the three sections 41–43 and then finally separated and trimmed in a cutting operation not illustrated herein. For the purpose of simplicity of description, the manual movement of the subassemblies through the three-step process is disclosed and individualized pieces of the layers 11–16 shown in FIGS. 8–18 in order to clarify the description of the assembly process and the resultant product produced therefrom. It will be obvious from reading the attached description that variations in the steps taken to assemble the neo-natal 1 probe 1 and the extents of the heat-sealing process at each step of this manufacturing process are matters of design choice, and variations therein would be obvious alternatives to the preferred embodiment disclosed herein and intended to be covered within the scope of the appended claims.

Manufacturing Process

Figure 8:
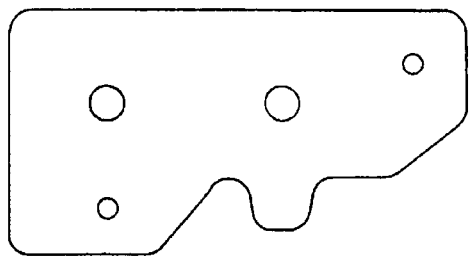
FIGS. 8–18 are top views of various component layers and combinations of component layers used in the manufacture of the neonatal probe of the present invention.
Figure 11:
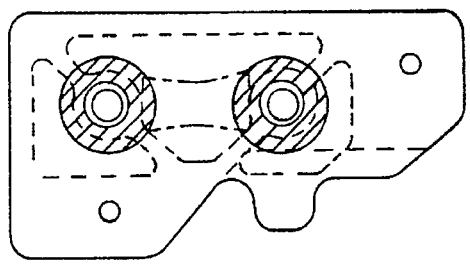
Figure 9:
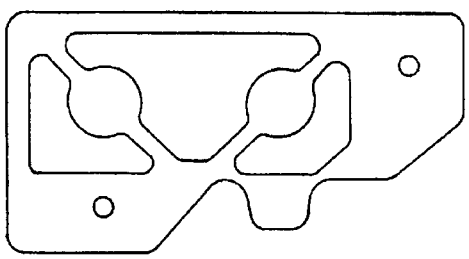
Figure 10:
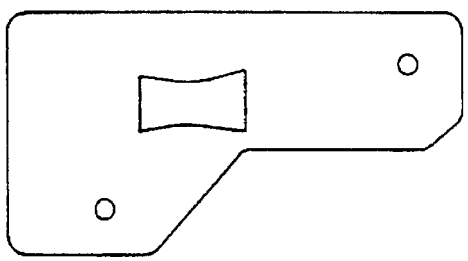

The first step of the manufacturing process is used to align and interconnect the various ones of layers 11–13 illustrated in FIG. 2 that are positioned between the light-emitting diodes 17, light detector 18 and the patient's skin. These layers 11–13 must be precisely aligned in order to provide optical paths for the light-emitting diodes 17 and light detector 18, to provide a thermally-insulative layer 13, the optically-insulating layer 12 as well as the adhesive layer 11 with which the resultant neo-natal probe 1 is affixed to the patient. The manufacturing process is initiated by placing the middle plate 32 (carrier) in the manufacturing apparatus 30 on top of the bottom plate 33. The middle plate 32 includes clearance holes 64–68 that mate with height stop alignment pins 44–48 in bottom plate 33 and height stop pins 34–38 in top plate 31. Land areas 41–43 on bottom plate 33 protrude through corresponding holes in the middle plate 32 so that top 31 and bottom 33 plates come into contact with the multiple layers of material yet leave room between plates to enable the material to flow when the heating elements are activated. The optically insulative material 13 includes a precut pair of optical ports 5, 6 and is placed on the first land area 41 of the middle plate 32 with the alignment pins 54, 55 passing through the apertures in the optically insulative layer 13 to provide precise alignment thereof. The next layer that is placed on the optically insulative layer 13 is the port cover layer 12. The two clear Kraton port covers 12 as illustrated in FIG. 2 are each interconnected by a pair of arms to the framework which includes a pair of apertures therein which align with the alignment pins 54, 55 in the middle plate 32 illustrated in FIGS. 3–7. Again, the implementation shown in FIG. 9 is a sheet of material with alignment apertures and differs from the final heat-sealed and die cut layer illustrated in FIG. 2. Finally, FIG. 10 illustrates the adhesive and release liner layer 11 with the integral adhesive attached thereto and a pair of alignment holes formed in the sheet material that implements the adhesive and release liner layer 11. The layers illustrated in FIGS. 8, 9 and 10 are placed successively one on top of the other on the middle plate 32 over the first land area 41 with the alignment pins 54, 55 of the middle plate 32 protruding through the respective apertures in these layers 11–13 to provide precise alignment of each of these layers 11–13 with respect to each other. The press 30 is then closed and the heat-seal element in the top plate 31 activated to stake these three layers 11–13 together by heat-sealing the periphery of the sensor element section 4 of the neo-natal probe 1. Alternatively, the layers 11–13 can be stacked in the reverse order described herein to create the subassembly.

Figure 12:
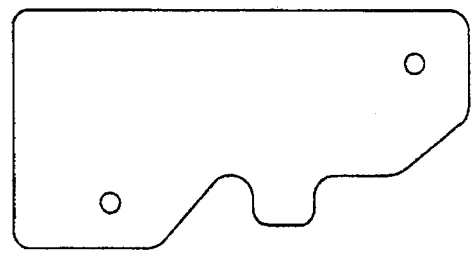
Figure 13:
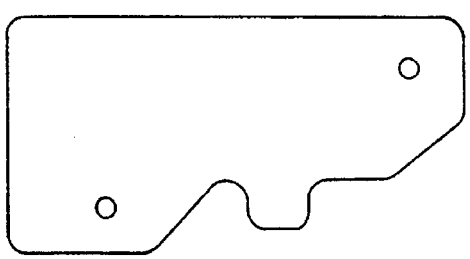
Figure 14:
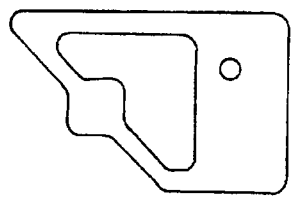
Figure 15:
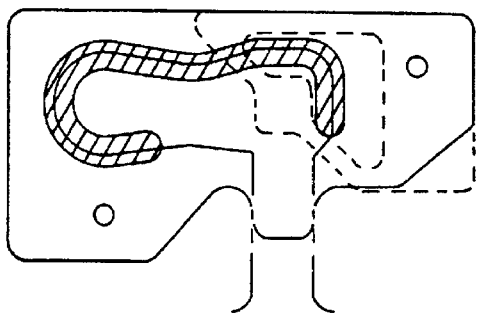
Figure 17:
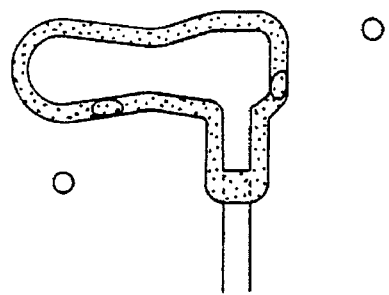

Once the heat-sealing element has been activated and functions to heat-seal these three layers 11–13 together, the press is opened and the subassembly is ready to be moved to the second section of the middle plate 32. Prior to movement of the subassembly, the bottom layers 15, 16 of the sensor element section 4 are placed in position on the middle plate 32. The coextrusion back cover 16 is illustrated in FIG. 12 and consists of a solid sheet of material with two alignment apertures formed therein. FIG. 13 illustrates the back opaque or translucent light dam layer 15 and consists of a continuous sheet of material with a pair of apertures formed therein. The final element in this stack of elements is the light-emitting diode thermal buffer layer 14 illustrated in FIG. 14 which consists of the buffer layer attached by two arms to a framework which includes a single alignment aperture formed therein. This is placed on top of the optically opaque or translucent layer 15 which is on top of the back cover layer 16. These three layers 14–16 are then overlaid with a subassembly transported from the first land area 41 of the die with the alignment apertures of all six layers 11–16 being fit over the alignment pins 56, 57 for the middle plate 32 which aligns over the second land area 42 of the bottom plate 33. The press 30 is then activated to sandwich the six layers 11–16 together and the heat-sealing element in the top plate 31 is activated to heat-seal approximately three-quarters of the periphery of what will be the resultant sensor element section 4 of the neo-natal probe 1. The extent of this heat-sealing operation is illustrated in FIG. 15 which illustrates a top view of the six-element package with the shaded area being indicative of the region that is heat-sealed by the second section of the die set. Again, the stack of elements 11–16 can be assembled in the reverse order described herein.

Figure 16:
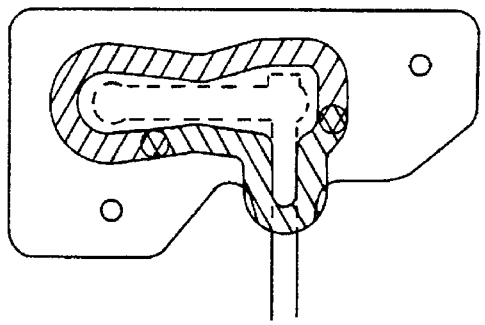
Figure 18:
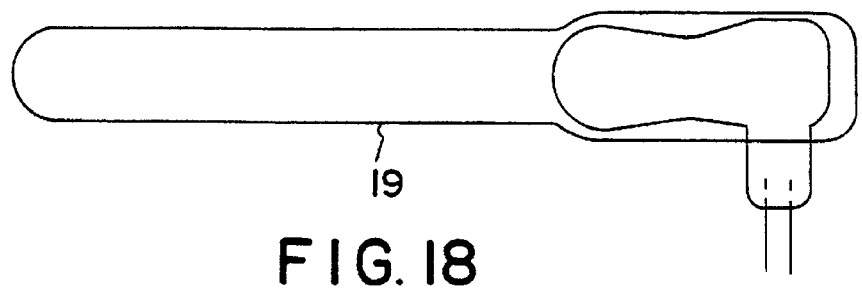

Once the heat-sealing operation is completed in this second stage of this three-stage process, the subassembly is ready to be moved to the third section of the die set. The subassembly is removed from the press 30 and the active elements 17, 18 inserted between the second 15 and third 14 layers of the six-layer subassembly as illustrated in FIG. 2. The middle plate 32 of the die set contains an opening 40 cut therein that corresponds to the cable 2 and light-emitting diodes 17 and light detector 18 elements. The second subassembly with the active elements 17, 18 and cable 2 inserted therein as shown in FIG. 16 is placed on third section of middle plate 32 with the alignment apertures of the six layers 11–16 of the subassembly placed over the alignment pins 58, 59 of the third section of the plate 32 in the configuration illustrated in FIG. 16. The press 30 is then again closed and the heat-sealing apparatus of the third section of the top plate 31 activated to complete the heat-sealing process and seal what is approximately one quarter of the periphery of the sensor element section 4 of the neo-natal probe 1. This remaining section of sealing is illustrated in shaded fashion on FIG. 16 to illustrate the extent of the heat-sealing required in this final step of the three-step assembly process. As can be seen from FIG. 16, the sensor element section 4 of the neo-natal probe 1 is now completely heat-sealed, including the entry point where the cable 2 enters the sandwich collection of layers illustrated in FIG. 2. The surplus material outside of the heat-sealed area may then be removed since this material is unnecessary to the operation of the neo-natal probe 1. A die cutting machine (not shown) can be used to trim this surplus material. The die cut includes a portion of the heat-sealed area to thereby ensure that the perimeter of the sensor element 4 of the neo-natal probe 1 is smooth without abrasive edges. The finally die-cut sensor section 4 of the neo-natal probe 1, shown in FIG. 17, then affixed to a larger bandage strap 19 as illustrated in FIG. 18 which wraps around the infant's foot to secure probe 1 in place. The final probe 1 consists of the plurality of layers 11–16 sealed together around the periphery in this embodiment although it is obvious that the heat sealing process can seal outer layers 11, 16 together around the periphery with the inner layers 12–15 being sealed together and affixed to at least one of the outer layers 11, 16.

It is expressly understood that the claimed invention is not to be limited to the description of the preferred embodiment but encompasses other modifications and alterations within the scope and spirit of the inventive concept.

We claim:

1. A method of manufacturing a heat-sealed monitoring probe which comprises a plurality of sensor elements and at least two outer layers of conformable material which substantially prevent interchange of fluids between an ambient environment extant around said probe and said plurality of sensor elements, said method comprising the steps of:

forming a first heat-sealed seam in a predetermined pattern substantially around a portion of the periphery of said at least two outer layers to form a pocket which is adapted to receive, enclose and secure said plurality of sensor elements in a predetermined position;

inserting said plurality of sensor elements in said pocket; and forming a second heat-sealed seam in a predetermined pattern, which joins with said first heat-sealed seam formed around said portion of the periphery of said at least two outer layers, to completely enclose said plurality of sensor elements within said pocket, isolated from said ambient environment.

2. The method of claim 1, wherein said step of forming a first heat sealed seam comprises:

placing said at least two outer layers of conformable material in a fixture for retaining said at least two outer layers of conformable material in predetermined position.

3. The method of claim 2, wherein said step of placing said at least two outer layers of conformable material in a fixture comprises:

placing a first of said at least two outer layers of conformable material in a fixture;

placing at least one inner layer of material in said fixture, aligned in predetermined position with respect to said first outer layer; and forming a third heat-sealed seam to join said first outer layer and said at least one inner layer into a subassembly.

4. The method of claim 3, wherein said step of forming said first heat-sealed seam comprises:

placing a second of said at least two outer layers in a fixture;

placing said subassembly in predetermined position with respect to said second outer layer; and activating a heating element to form said first heat-sealed seam to join said second outer layer and said subassembly.

5. The method of claim 3, wherein said step of forming said first heat-sealed seam comprises:

placing a second of said at least two outer layers in a fixture;

placing at least one inner layer in predetermined position with respect to said second outer layer;

placing said subassembly in predetermined position with respect to said second outer layer; and activating a heating element located in said fixture to form said first heat-sealed seam to join said second outer layer, said at least one inner layer, and said subassembly.

6. The method of claim 2, wherein said plurality of sensor elements are connected to a first end of a plurality of electrical conductors, said step of placing comprises:

inserting said plurality of sensor elements, including a length of said plurality of electrical conductors proximate said first end into said pocket.

7. The method of claim 6 wherein said step of forming a second heat-sealed seam forms a heat-sealed seam around said plurality of electrical conductors where said plurality of electrical conductors exit said pocket.

8. The method of claim 1 further comprising the step of:

removing at least a portion of said at least two outer layers of conformable material which extends outwardly beyond said second heat-sealed seam.

9. A method of manufacturing a heat-sealed monitoring probe which comprises a plurality of sensor elements connected to a first end of a plurality of electrical conductors and at least two outer layers of conformable material which substantially prevent interchange of fluids between an ambient environment extant around said probe and said plurality of sensor elements, said method comprising the steps of:

placing said at least two outer layers of conformable material in a fixture for retaining said at least two outer layers of conformable material in predetermined position;

forming a first heat-sealed seam in a predetermined pattern substantially around a portion of the periphery of said at least two outer layers of conformable material to form a pocket which is adapted to receive, enclose and secure said plurality of sensor elements in a predetermined position;

inserting said plurality of sensor elements, including a length of said plurality of electrical conductors proximate said first end into said pocket; and forming a second heat-sealed seam in a predetermined pattern, which joins with said first heat-sealed seam formed around said portion of the periphery of said at least two outer layers, around said plurality of electrical conductors where said plurality of electrical conductors exit said pocket to completely enclose said plurality of sensor elements within said pocket, isolated from said ambient environment.

10. The method of claim 9, wherein said fixture includes a plurality of projections which correspond in geometry to openings formed in said at least two outer layers of conformable material, said step of placing said at least two outer layers of conformable material in a fixture comprises:

positioning said at least two layers of conformable material to place said openings formed in at least two outer layers of conformable material on said projections to retain said at least two outer layers of conformable material in predetermined position.

11. The method of claim 9, wherein said fixture includes a plurality of projections which correspond in geometry to openings formed in said at least two outer layers of conformable material, said step of placing said at least two outer layers of conformable material in a fixture comprises:

positioning a first of said at least two layers of conformable material to place said openings formed in said first outer layer of conformable material on said projections to retain said first outer layer of conformable material in predetermined position in said fixture;

positioning at least one inner layer of material to place openings formed in said at least one inner layer of material on said projections to retain said at least one inner layer of material in predetermined position aligned in predetermined position with respect to said first outer layer; and forming a third heat-sealed seam to join said first outer layer and said at least one inner layer into a subassembly.

12. The method of claim 11, wherein said fixture includes a heating element, said method of forming a third heat-sealed seam comprises:

activating said heating element to meltably merge said first outer layer with said at least one inner layer along said third heat-sealed seam.

13. The method of claim 11, wherein said step of forming said first heat-sealed seam comprises:

positioning a second of said at least two layers of conformable material to place said openings formed in said second outer layer of conformable material on said projections to retain said second outer layer of conformable material in predetermined position in said fixture;

positioning said subassembly to place said openings formed in said first outer layer of conformable material on said projections to retain said subassembly in predetermined position with respect to said second outer layer; and activating a heating element located in said fixture to form said first heat-sealed seam to join said second outer layer and said subassembly.

14. The method of claim 11, wherein said step of forming said first heat-sealed seam comprises:

positioning a second of said at least two layers of conformable material to place said openings formed in at least two outer layers of conformable material on said projections to retain said second outer layers of conformable material in predetermined position in said fixture;

positioning at least one inner layer of material to place said openings formed in said at least one inner layer of material on said projections to retain said at least one inner layer of material in predetermined position with respect to said second outer layer;

positioning said subassembly to place said openings formed in said first outer layer of conformable material on said projections to retain said subassembly in predetermined position with respect to said second outer layer; and activating a heating element located in said fixture to form said first heat-sealed seam to join said second outer layer, said at least one inner layer, and said subassembly.

15. The method of claim 9 further comprising the step of:

removing at least a portion of said at least two outer layers of conformable material which extends outwardly beyond said second heat-sealed seam.

16. The method of claim 9, wherein said fixture includes a plurality of heating elements and a plurality of projections which correspond in geometry to openings formed in said at least two outer layers of conformable material, said step of placing said at least two outer layers of conformable material in a fixture comprises:

positioning a first of said at least two layers of conformable material to place said openings formed in said first outer layer of conformable material on said projections to retain said first outer layer of conformable material in predetermined position in said fixture with respect to a first of said plurality of heating elements;

positioning at least one inner layer of material to place openings formed in said at least one inner layer of material on said projections to retain said at least one inner layer of material in predetermined position aligned in predetermined position with respect to said first outer layer; and activating said first heating element to form a third heat-sealed seam to join said first outer layer and said at least one inner layer into a subassembly.

17. The method of claim 16, wherein said step of forming said first heat-sealed seam comprises:

positioning a second of said at least two layers of conformable material to place said openings formed in said second outer layer of conformable material on said projections to retain said second outer layer of conformable material in predetermined position in said fixture with respect to a second of said plurality of heating elements;

positioning said subassembly to place said openings formed in said first outer layer of conformable material on said projections to retain said subassembly in predetermined position with respect to said second outer layer; and activating said second heating element located in said fixture to form said first heat-sealed seam to join said second outer layer and said subassembly.

18. The method of claim 17, wherein said step of forming said second heat-sealed seam comprises:

positioning said subassembly joined to said second outer layer to place said openings formed in said second outer layer of conformable material on said projections to retain said subassembly joined to said second outer layer in predetermined position in said fixture with respect to a third of said plurality of heating elements; and activating said third heating element located in said fixture to form said second heat-sealed seam.

19. The method of claim 18 further comprising the step of:

removing at least a portion of said at least two outer layers of conformable material which extends outwardly beyond said second heat-sealed seam.

* * * * *